United States Patent
Mohr et al.

(10) Patent No.: US 7,258,439 B2
(45) Date of Patent: Aug. 21, 2007

(54) DEVICE FOR IMAGING AND OBSERVING AN EYE AT A SELECTABLE IMAGE SCALE

(75) Inventors: Thomas Mohr, Jena (DE); Detlef Biernat, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 10/559,167

(22) PCT Filed: May 28, 2004

(86) PCT No.: PCT/EP2004/005767

§ 371 (c)(1),
(2), (4) Date: Dec. 1, 2005

(87) PCT Pub. No.: WO2004/107967

PCT Pub. Date: Dec. 16, 2004

(65) Prior Publication Data
US 2006/0170866 A1 Aug. 3, 2006

(30) Foreign Application Priority Data
Jun. 6, 2003 (DE) ................. 103 26 510

(51) Int. Cl.
*A61B 3/14* (2006.01)
(52) U.S. Cl. .................................... 351/206
(58) Field of Classification Search ............... 351/206, 351/205
See application file for complete search history.

(56) References Cited
U.S. PATENT DOCUMENTS 5,841,509 A * 11/1998 Harooni et al. ............. 351/221
6,296,358 B1 * 10/2001 Cornsweet et al. ......... 351/206
6,361,167 B1 * 3/2002 Su et al. ..................... 351/206

FOREIGN PATENT DOCUMENTS

| DE | 24 35 548 | 5/1975 |
| DE | 195 24 498 | 1/1997 |
| DE | 101 38 158 | 2/2003 |

* cited by examiner

*Primary Examiner*—Scott J. Sugarman
(74) *Attorney, Agent, or Firm*—Reed Smith LLP

(57) ABSTRACT

The present invention is directed to a device for examining the eye, preferably the fundus of the eye, by an optical system and electronic sensors for image recording in different imaging scales. In the device according to the invention, at least two image recording sensors with different shape factors are swivelably arranged in the imaging plane of the device. These image recording sensors have optically active surfaces of different geometric sizes, an approximately identical number of pixels and preferably the same electronic control and evaluation. The invention described herein requires no additional objectives and the optical adjustment is limited to an individual rigid objective. An exact alignment of the image recording sensors in the imaging plane and manufacturing tolerances can be compensated by adapting the image section by means of software. It is particularly advantageous that the imaging scale is influenced without changing the optical parameters of the system.

4 Claims, 1 Drawing Sheet

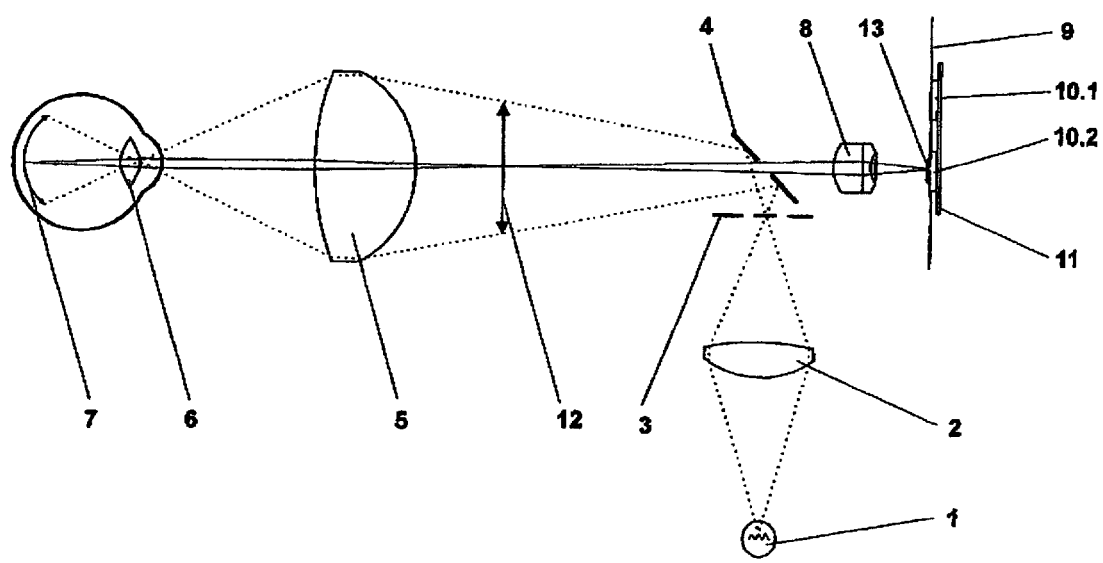

DEVICE FOR IMAGING AND OBSERVING AN EYE AT A SELECTABLE IMAGE SCALE

CROSS-REFERENCE TO RELATED APPLICATIONS

This application claims priority of International Application No. PCT/EP2004/005767, filed May 28, 2004, and German Application No. 103 26 510.4, filed Jun. 6, 2003, the complete disclosures of which are hereby incorporated by reference.

BACKGROUND OF THE INVENTION a) Field of the Invention

The present invention is directed to a device for examining the eye, preferably the fundus of the eye, by means of an optical system and electronic sensors for image recording, wherein sectional enlargements of the recordings are possible by means of changing the imaging scale.

b) Description of the Related Art

According to the known prior art, the imaging scale in devices of the type mentioned above is usually changed by optical means which are swiveled into and out of the beam path in addition to or in exchange with one another.

The Laid Open Application DE 24 35 548 describes an optical system for photographing the retina with selectable imaging scale in which a plurality of optical changing systems which can be introduced into the beam path individually are provided in addition to the stationary objective systems. These changing systems are axially displaceable together with the aperture diaphragm in order to carry out focusing for eyes with defective vision. This technical solution is realized, for example, in the "FF 450" fundus camera by Carl Zeiss Meditec AG.

The disadvantage of this application consists primarily in the complicated adjustment of the optics and in the fact that the mechanical movement must be carried out very exactly. Since a complete set of optical components is required for every imaging scale, the structural size of the device in its entirety is substantially influenced by the size of the objective turret.

A simple technical solution for digital observation and documentation of the ocular fundus without eyepieces is offered by the "VISUCAM lite" fundus camera by Carl Zeiss Meditec AG. In this fundus camera, a black-and-white sensor and a color sensor are alternately laterally swiveled into the imaging plane of the system. In addition to the color photographs, black-and-white photographs are made using different monochrome techniques (red-free, blue, red) due to a higher sensitivity. To facilitate their comparison, the sensors have identical shape factors. By virtue of its many-sided possibilities for recording, analysis and aftertreatment, this solution provides a basic instrument for ophthalmologic practice and laser treatment.

The disadvantage in this device is that it does not provide for changing the optical imaging scale. In order to achieve this, an additional objective turret would be required. A correction of defective vision (also referred to as focusing) is carried out by a mechanical movement of the sensors along the optical axis.

OBJECT AND SUMMARY OF THE INVENTION

It is the primary object of the present invention to develop a solution for displaying and observing an eye in which imaging scales are selectable without making the basic construction of the device overall substantially more complicated and bulky. Further, the effort required for adjustment and assembly is minimized.

According to the invention, this object is met by a device for displaying and observing an eye with selectable imaging scale comprising image recording sensors with different shape factors which are swivelably arranged in an imaging plane.

With the proposed technical solution, image sections of the eye and of the fundus of the eye in particular can be observed and documented in different sizes.

The invention will be described in the following with reference to an embodiment example.

BRIEF DESCRIPTION OF THE DRAWING

In the drawing:

FIG. 1 shows the basic construction of the device according to the invention in a fundus camera.

DESCRIPTION OF THE PREFERRED EMBODIMENTS

In the device according to the invention for displaying and observing an eye with selectable imaging scale, at least two image recording sensors with different shape factors are swivelably arranged in the imaging plane of the device.

The different shape factors can be realized by optically active surfaces of the image recording sensors of identical geometrical size with a different quantity of pixels. The image recording sensors which are swivelably arranged in the imaging plane preferably have an approximately identical numbers of pixels with optically active surfaces of different sizes. This has the advantage that the electronic control and evaluation for the image recording sensors are identical.

The image recording sensors arranged in the imaging plane can be introduced into the beam path by a lateral movement as well as by a circular movement. The cable feed is considerably simplified in the case of a lateral movement.

FIG. 1 shows the basic construction of the device according to the invention. In the illumination beam path, the light coming from the light source 1 is guided to the ocular fundus 7 via the illumination optics 2, the diaphragm for the annular illumination aperture 3, the pinhole mirror 4, the ophthalmoscope lens 5 and the eye lens 6. The fundus 7 which is illuminated in this way is imaged in the imaging plane 9 via the ophthalmoscope lens 5 through the pinhole mirror 4 via the principal objective 8. According to the invention, at least two swivelable image recording sensors 10.1 and 10.2 are arranged in the imaging plane 9 on a common carrier 11. In the imaging beam path, a first intermediate image 12 is generated between the ophthalmoscope lens 5 and the pinhole mirror 4 and a second intermediate image 13 is generated in the imaging plane 9. This imaging plane 9 is located at a variable distance from the main objective 8 depending on the defective vision of the eye being examined. Focusing is necessary in order to achieve a sharp image on one of the image recording sensors 10.1 or 10.2. Focusing is carried out by axial displacement of the carrier 11 so that one of the image recording sensors 10.1 or 10.2 is located in the imaging plane 9. The different magnification steps for display and observation are realized by swiveling in another image recording sensor 10.1 or 10.2.

The change in the imaging scale is carried out by means of swiveling image recording sensors with different shape factors into the imaging plane of the ophthalmic instrument.

The image recording sensors have an approximately identical number of pixels, but have optically active surfaces of different geometric sizes. Accordingly, the imaging scale is influenced without changing the optical parameters of the system.

No additional objectives are required for this purpose in the described invention. The optical adjustment is limited to an individual rigid objective. Precise mechanical guidance and the movement of a plurality of objectives are no longer necessary. Even an exact alignment of the image recording sensors in the imaging plane is not absolutely necessary because they can be compensated by adapting the image section by means of software. This also applies to manufacturing tolerances.

It is particularly advantageous that the imaging scale is influenced without changing the optical parameters of the system. Accordingly, image sections of the eye and of the fundus of the eye can be observed, recorded, reworked and stored in different sizes.

While the foregoing description and drawings represent the present invention, it will be obvious to those skilled in the art that various changes may be made therein without departing from the true spirit and scope of the present invention.

What is claimed is:

1. A device for displaying and observing an eye with selectable imaging scale, comprising a plurality of image recording sensors with different shape factors being swivelably arranged in an imaging plane for recording images in a single beam path.

2. The device according to claim 1, wherein the image recording sensors which are swivelably arranged in the imaging plane have an approximately identical number of pixels and operated by the same electronic control and evaluation unit.

3. The device according to claim 1, wherein the image recording sensors arranged in the imaging plane are introduced into a beam path by a lateral movement.

4. The device according to claim 1, wherein the image recording sensors arranged in the imaging plane are introduced into a beam path by a circular movement.

* * * * *